United States Patent [19]

Goldberg et al.

[11] Patent Number: 4,689,302
[45] Date of Patent: Aug. 25, 1987

[54] SPIRAL DESIGNED REACTOR

[75] Inventors: Bruce S. Goldberg, Clifton; Richard Chen, Livingston, both of N.J.

[73] Assignee: Amerace Corporation, Hackettstown, N.J.

[21] Appl. No.: 595,954

[22] Filed: Apr. 2, 1984

[51] Int. Cl.[4] .............................................. C12M 1/40
[52] U.S. Cl. .................................... 435/288; 435/287
[58] Field of Search .................... 422/70, 71; 435/287, 435/288, 813

[56] References Cited

U.S. PATENT DOCUMENTS

| 3,746,550 | 7/1973 | Ehnstrom | 435/813 X |
| 3,812,016 | 5/1974 | Muller | 435/285 |
| 3,853,712 | 12/1974 | House et al. | 435/313 X |
| 4,033,825 | 7/1977 | Haddad et al. | 435/313 X |
| 4,292,409 | 9/1981 | Cremonesi | 435/288 |

FOREIGN PATENT DOCUMENTS 58-56671 4/1983 Japan .................................. 435/288

Primary Examiner—Samuel Scott
Assistant Examiner—Allen J. Flanigan
Attorney, Agent, or Firm—David Teschner

[57] ABSTRACT

A flow reactor for reacting a feedstock with a proteinaceous preparation immobilized on and within the pores of a support medium while traversing a spiral path between adjacent turns of said spiral. A support medium has a spacing means placed on one surface thereof. The support medium and spacing means are then wound upon a porous core to form a jelly roll-like spiral configuration. The marginal edges of the reactors are sealed but provision is made to introduce or remove materials from said core and the free end of the spiral is left open to also introduce or remove materials. In a first form the feedstock is introduced into the core and the reacted feedstock is removed from the spiral free end. In a second form the introduction and removal of the feedstock and reacted feedstock is reversed. The spacing means may be a series of ribs on the support medium or may be a net-like sheet.

10 Claims, 9 Drawing Figures 4,689,302

SPIRAL DESIGNED REACTOR

BACKGROUND OF THE INVENTION

1. Field of the Invention

The invention is directed to the field of chemical reactors wherein a feedstock is converted to more desirable product by the interaction of the feedstock with a proteinaceous preparation affixed on or within the pores of a support medium which defines the reactor format.

2. Description of the Prior Art

In known flow through reactors it is well known that materials which include large particles or which will coagulate in the presence of immobilized proteinaceous preparations will impede the functioning of the reactor. Accordingly, provision must be made to remove these particles prior to introduction to the reactor or the reactor must be frequently backwashed to remove the particles or coagulants. In the former case a filtration system must be used before the reactor stage. For example in the processing of whey an ultrafiltration system is used to remove the fat globules, protein, cheese solids in the whey before introduced to the reactor. In the later case when wort is fermented in the making of beer, the flow of the wort must be periodically interrupted to permit the spent enzyme carrier to be backwashed from the reactor so that the beer wort can thereafter flow through the reactor.

In each of these approaches additional equipment and time is required depriving the user of all the benefits available in a flow-through system.

One approach to a spiral form of reactor is shown in U.S. Pat. No 4,292,409 issued Sept. 29, 1981. In this patent a thin spiral channel is formed on one semi-block and the enzyme is immobilized on a second flat semi-block. The two semi-blocks are then joined, and the material to be treated is passed through the spiral channel. Contact with the immobilized enzyme can only occur along the narrow planar surface bounding the spiral channel. Because of the minimal contact between the feedstock and the enzyme only limited conversion of the feedstock can occur. U.S. Pat. No 3,809,613 issued May 7, 1974 to Vieth shows a membrane, such as a collagen with an enzyme entrapped in the collagen wrapped about a series of spacer rods and having the general appearance of a spiral. However, the flow is across only one face of the membrane and extends transverse to the spiral rather than along the spiral path.

SUMMARY OF THE INVENTION

The spiral reactor of the instant invention overcomes the difficulties noted above with respect to prior art devices by permitting a flow system without the need to filter the materials introduced to the reactor or requiring shut down of the reactor to backwash same. Further, since almost all of the surfaces defining the passage have the proteinaceous preparations immobilized thereon the feedstock is able to contact both active surfaces, that have the proteinaceous preparations on them, unlike prior art designs in which the feedstock contacts only a single active surface, and which results in a higher rate of conversion of the feedstock. This is accomplished by taking a support medium having a first surface and a second surface and a plurality of pores, the surfaces having a proteinaceous preparation immobilized on and within said pores. Upon said second surface is positioned a spacing means which may be in the form of a series of longitudinal ribs on said second surface or a separate net-like sheet placed atop said second surface of support medium. The stacked support medium and spacing means is then rolled up upon a pourous core to form a jelly roll-like spiral reactor. The marginal edges of the reactor are sealed to prevent the materials within the reactor exiting before the end of the reactor is reached. Access is provided from the outside into the core and also to the free end of the spiral configuration. The feedstock can be introduced through the core and the reacted feedstock removed from the free end of the reactor or visa versa. It is therefore an object of this inveniton to provide an improved reactor.

It is another object of this invention to provide a reactor wherein the feedstock introduced into the reactor does not have to be filtered prior to introduction.

It is another object of this invention to provide a reactor which does not have to be regularly backwashed to free its surface of particles or partially reacted feedstock to maintain a sufficient flow through the reactor.

It is still another object of this invention to provide a reactor whose defining walls are substantially covered with the proteinaceous preparation required to convert the feedstock.

It is yet another object of this invention to provide a reactor in the form of a jelly roll-like spiral configuration.

It is another object of this invention to provide a reactor in the form of a jelly roll-like spiral configuration wherein substantially all of the convolutions thereof are separated from adjacent convolutions by a predetermined amount.

It is another object of this invention to provide a reactor in the form of a jelly roll-like spiral configuration wherein substantially all of the convolutions thereof are separated from adjacent convolutions by a series of raise ribs on one surface of said reactor.

It is yet another object of this invention to provide a reactor in the form of a jelly roll spiral configuration wherein substantially all of the convolutions thereof are separated from adjacent convolutions by a layer of net-like sheeting on one surface of said reactor.

Another object of this invention is to provide a reactor in the form of a jelly roll spiral configuration wherein the marginal edges of said reactor is sealed to prevent exit of the feedstock or converted feedstock prior to its desired exit.

It is yet another object of this invention to provide a reactor in the form of a jelly roll spiral configuration wound upon a porous core and having its marginal edges sealed, wherein feedstock introduced within said porous core is converted and exits at the free end of said spiral.

It is still another object of this invention to provide a reactor in the form of a jelly roll spiral configuration wound upon a porous core and having its marginal edges sealed, wherein feedstock introduced at the free end of said spiral is converted and exits at said porous core.

It is yet another object of this invention to teach the method of making an improved jelly roll spiral configuration reactor.

Other objects and features of the invention will be pointed out in the following description and claims and illustrated in the accompanying drawings, which disclose, by way of example, the principles of the invention, and the best modes which have been contemplated for carrying them out.

BRIEF DESCRIPTION OF THE DRAWINGS:

In the drawings in which similar elements are given similar reference characters.

DESCRIPTION OF THE PREFERRED EMBODIMENTS

Figure 1:
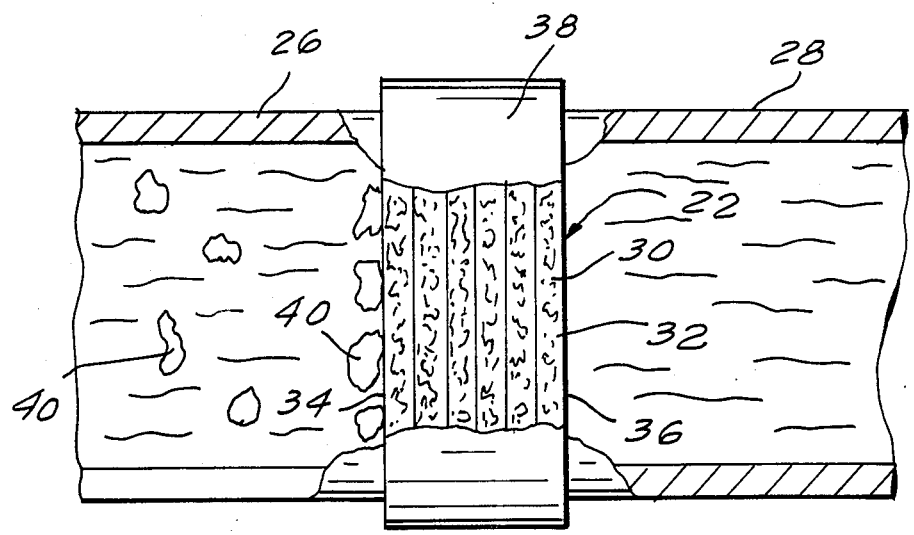
FIG. 1 is fragmented, sectioned, highly enlarged and idealized side elevation of a flow-through reactor of the type known in the prior art.
Figure 2:
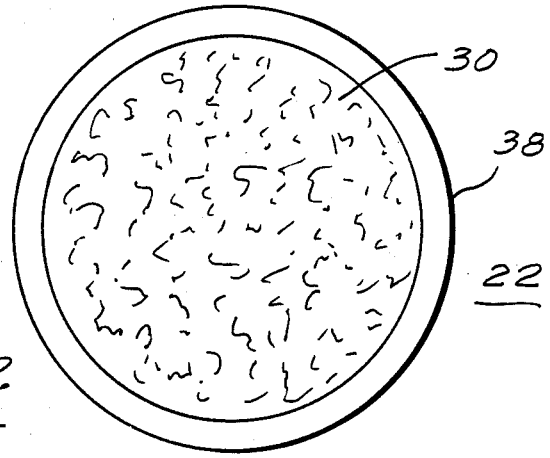
FIG. 2 is a front view of the reactor only of FIG. 1.
Figure 3:
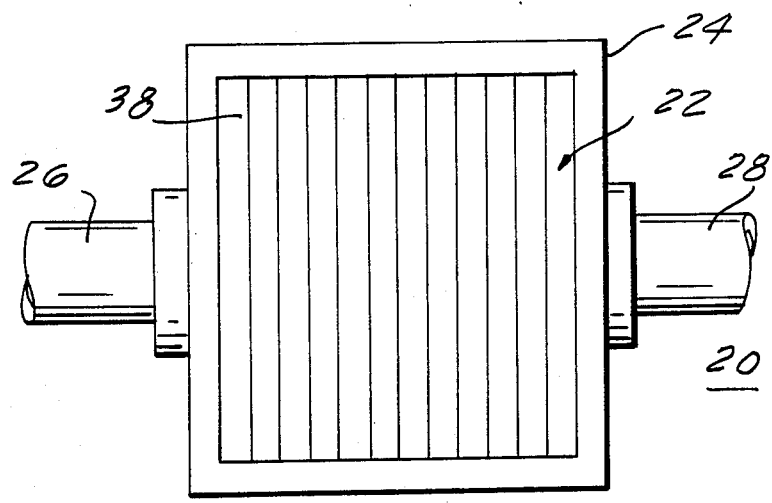
FIG. 3 is a side elevation of a reactor system containing a plurality of reactors of the type shown in FIGS 1 and 2 together with accessory supports and piping.

Turning now to FIGS. 1 to 3 a typical flow-through reactor system of the type known in the prior art is shown. Reactor system 20, as best seen in FIG. 3, is comprised of a plurality of reactor modules 22 in a support frame 24 having an input pipe 26 for supplying the feedstock stock and an output pipe 28 for removing the converted feedstock. Ducts within frame 24 (not shown) serve to distribute the feedstock over the full surface of reactor modules 22 and collect the converted feedstock emerging over the entire surface of such reactor modules 22.

As is best seen in FIGS. 1 and 2, each reactor module 22 comprises a plurality of stacked microporous sheets 30 having a plurality of pores 32 extending from surfaces 34 and 36 of the sheets 30 (See FIG. 1). These pores 32 are not continuous, but rather form a random tortuous pathway. One type of microporous sheet 30 is shown and described in U.S. Pat. No 4,102,746 issued July 25, 1978 in the name of Bruce S. Goldberg and assigned to the assignee of the instant invention. In addition other plastic and rubber sheets can be used.

Proteinaceous preparations, for example enzymes, can be immobilized upon the silica fragments on the surface of the sheeting and in the pores of the sheeting employing the techniques described in the U.S. Pat. No. 4,102,746 and in U.S. Pat. No 4,169,014 issued Sept. 25, 1979 in the name of Bruce S. Goldberg and also assigned to the assignee of the instant invention. Other suitable techniques are also known in the prior art.

The marginal edges as well as small portions of the front and back sheets 30 are sealed by a suitable plastic or rubber annular collar 38 which serves to retain the reactor module 22 as an integral unit and prevents the leaking of the feedstock or coverted feedstock from the reactor module 22 in a direction other than that desired.

Because of the pore 32 size being in the range of 0.01 microns to 100 microns, the presence of fat globules, protein, cheese solids and any materials which can coagulate to form globules and can quickly seal the pores 32 and reduce or completely cut off any flow through the reactor system 20 showing the use of a single reactor module 22. The feedstock introduced through input pipe 26 has a number of fat globules 40 disbursed therein. Since these globules 40 are larger than the pore 32 size, either alone or with a number combined, they soon coat the surface 34 and prevent any of the feedstock from entering into the pores 32. As set forth above these globules 40 must be removed by filtration of the feedstock before it is introduced into the reactor system 20 or periodically the feedstock stream must be stopped and the reactor system 20 backwashed by the use of suitable material, such as water, and causing it to flow from surface 36 to surface 34 against the normal flow through the reactor system 20, that is from surface 34 to surface 36. Both of these approaches are expensive and time consuming and very undesirable in that it increases the cost of the converted feedstock.

Figure 4:
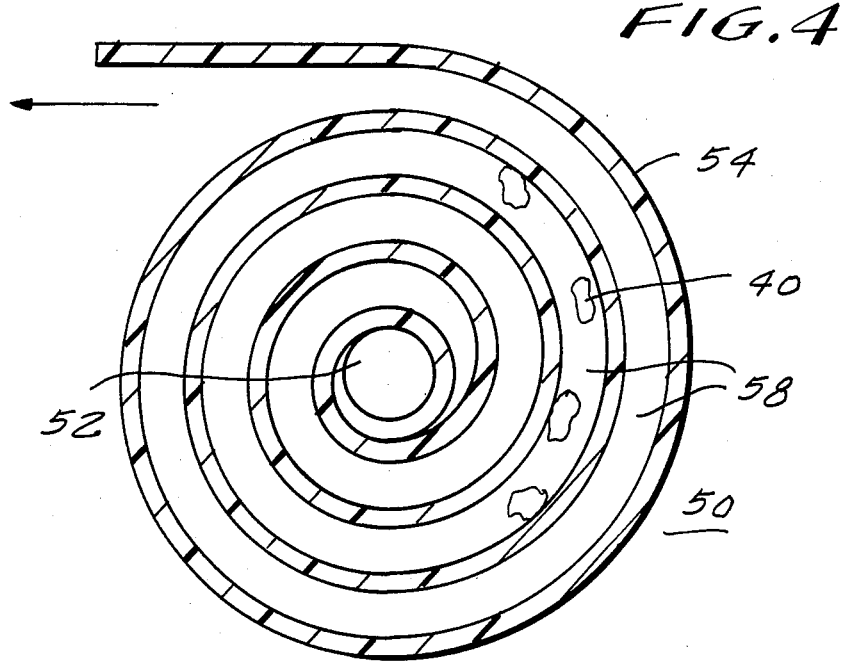
FIG. 4 is a side elevation, in section, of a jelly roll spiral configuration reactor constructed in accordance with the concepts of the invention and with the spacing layer omitted for the sake of clarity.
Figure 5:
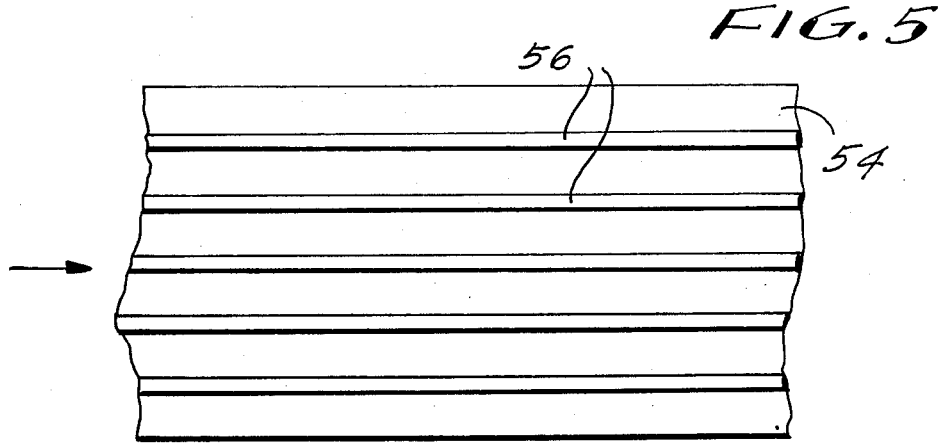
FIG. 5 is a fragmentary bottom plan view of a material from which the spiral reactor of FIG. 4 is formed and showing the ribs formed on one surface thereof.
Figure 6:
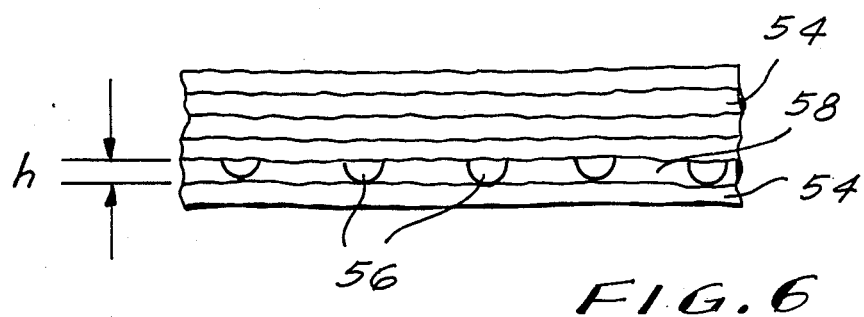
FIG. 6 is a front elevational view of a portion of the spiral reactor of FIG. 4 and showing the manner in which the ribs on one surface of the material keep adjacent convolutions of the reactor separated.

Turning now to FIG. 4 there is shown a spiral reactor 50 constructed in accordance with the concepts of the invention. The reactor 50 comprises a porous core 52 of appropriate diameter and volume that it can accept the feedstock introduced into the reactor 50 or to receive the converted feedstock to conduct it from the reactor 50. As in the flow-through reactor 20, the spiral reactor 50 is predominantly made up of microporous sheets 54 having a proteinaceous preparation immobilized on or in the pores of the sheets 54. However, the sheets 54 are modified to include a plurality of longitudinal ribs 56 on one surface thereon as is shown in FIGS. 5 and 6. The ribs 56 contact the adjacent convolutions of the spiral to keep them separated and to establish a series of passages 58 therebetween in conjunction with the spiral convolutions themselves. The height h (see FIG. 6) is so chosen that a desired flow through reactor 50 is attained while insuring proper conversion of the feedstock. The height h of the ribs 56 has been found to be in the range of 0.005" to 0.030" and most particularly about 0.010". The height will, of course, have to be altered depending upon the feedstock employed. the total space available for feedstock flow is identified as the void volume and measured in cubic centimeters.

Figure 7:
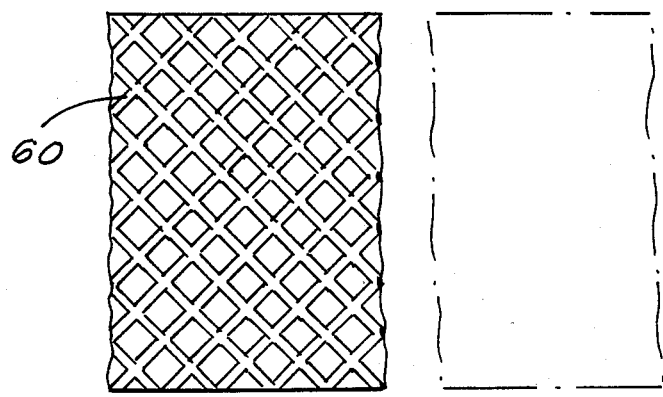
FIG. 7 is a fragmentary top plan view of a net-like spacing sheet which can be used with the support medium to construct a reactor in accordance with the concepts of the invention.
Figure 8:
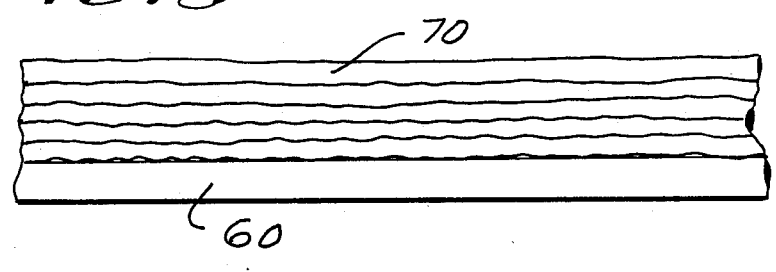
FIG. 8 is a fragmentary side elevation of the spacing sheet of FIG. 7 positioned adjacent one surface of the support medium.

Alternatively, a spacing sheet 60 as shown in FIGS. 7 and 8 may be employed instead of the raised ribs 56. The spacing sheet 60 is made of a flexible plastic or rubber material and in an open fish net format to assure light weight and flexibility. Spacing sheet 60 is simply laid atop a microporous sheet 70 as shown in FIG. 8. Even though the surfaces of the spacing sheet 60 are substantially flat, the surface of the sheeting is not. The spacing sheet 60 will rest on a number of peaks on the surface of sheet 70, providing, along with the open net format of the sheet 60 sufficient passages to permit the feedstock to pass the spacing sheet 60.

Figure 9:
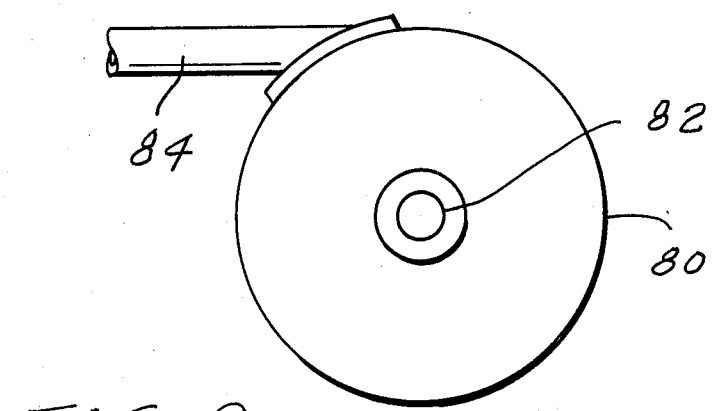
FIG. 9 is a simplified side elevational view of the completed reactor with inlet and outlet pipes connected thereto.

The reactor 50 is completed as shown in FIG. 9 by encapsulating the entire unit in a suitable housing 80. A pipe 82 is provided to gain access to the core 52 and plenum 84 is to provide access to the free end of the reactor. Although it is preferable to introduce the feedstock under suitable pressure into the core 52 of the reactor 50 and remove the converted feedstock from the free end 56 of the reactor 50, the opposite flow pattern can also be used, namely introduce the feedstock to the free end 56 and remove the converted feedstock from core 52.

The microporous sheeting together with a spacing layer, whether ribs 56 or spacing sheet 60 are wound upon core 52 to form the spiral configuration shown in FIG.4. As the feedstock flows along the passage 58 it is sufficiently exposed to enzyme to convert the feedstock to a high degree.

The spiral reactor 50 may be formed of a stack of individual microporous sheets 54 0.020 inches thick or by winding on itself a 90 inch length of 0.020 inch thick microporous material to produce a layer 1 inch thick and having a width of 3 inches. Considering that both sides of the sheets 54 are available a total surface area of 270 square inches, reduced by the areas of contact of the sheet 54 edges with the housing 80, 240 square inches of surface is effective. Employing ribs 56 having a height h of 0.010 inches and winding the sheets 54 on a porous core 52, 1 inch in diameter and 3 inches long, results in a reactor 50 having an outside diameter of 2 inches and a void volume or flow path volume of between 30 and 40 cubic centimeters. When potted, that is with the housing 80 in place the outside diameter is $2\frac{3}{4}$ inches thick.

With the enzyme lactase immobilized on the sheets 54, as set out in U.S. Pat. No 4,169,014 identified above, and employing skim milk adjusted to a pH of 5.1 at a flow rate of 10 milliliters per minute at 40° C. with a residence time of 3 to 4 minutes, reactor 50 is capable of hydrolyzing 90% of the lactose in the skim milk.

If a reactor 50 is constructed using a spacing sheet 60 of a fish net format having open areas equivalent to 70% of the area if a continuous sheet of the same dimensions and a thickness of 0.010 inches, the available void volume will be 50 cubic centimeters. Using the same feedstock under the same conditions set out in the previous example, approximately the same percentage of lactose in the skim milk will be hydrolyzed. It has been found that in actual practice conversions of the feedstock has reached values as high as 90%. The path through the reactor 50 is assumed generally to be laminar, but in practice it has been found to have a random flow, produce eddys and in some cases may also pass through the sheeting 54.

While there have been shown and described and pointed out the fundamental novel features of the invention as applied to the preferred embodiments, it will be understood that various omissions and substitutions and changes of the form and details of the devices illustrated and in their operation may be made by those skilled in the art, without departing from the spirit of the invention.

The embodiments of the invention in which an exclusive property or privilege is claimed are defined as follows:

1. A flow reactor for reacting a feedstock directly with a proteinaceous preparation immobilized on and within the pores of a support medium comprising:
    a support medium having a thickness in the range of about 15 mils to about 35 mils and a first surface and a second surface and a plurality of random pores having pore sizes in the range of about 0.01 micron to about 100 microns; flexible spacing means; porous core means; said spacing means positioned upon said second surface of said support means and both said support means and said spacing means wound about said core means to form a jelly roll-like spiral configuration wherein said support means is not folded upon itself prior to being wound about said core means to cause the feedstock and reacted feedstock to follow along and between the turns of said support means; first means coupled to said core means and second means coupled to the free end of said spiral configuration.

2. A reactor as defined in claim 1 further comprising; first coupling means coupled to second means to introduce a feedstock to said reactor through the free end of said spiral configuration and second coupling means coupled to said first means to remove the reacted feedstock from said reactor through said core means.

3. A reactor as defined in claim 1, wherein said spacing means is formed as a series of longitudinal ribs on said second surface of said support medium which engage said first surface of said support medium as said support medium and spacing means is wound into its spiral configuration.

4. A reactor as defined in claim 3, wherein said ribs have a height from about 0.005" to 0.030".

5. A reactor as defined in claim 1, wherein said spacing means comprises: a sheet material having a generally net-like configuration which rests non-uniformly upon said second surface of said support medium and non-uniformly contacts said first surface of said support medium as said support medium and said spacing means is wound into its spiral configuration.

6. A reactor as defined in claim 1, wherein the marginal edges of said support medium and spacing means wound into its spiral configuration are sealed to prevent exit from the reactor at said edges; port means in said seal to permit external access to said core means by said first means to said free end of said spiral configuration by said second means.

7. A reactor as defined in claim 5, wherein said sheet material has a thickness from about 0.005" to 0.003".

8. The method of forming a flow reactor for reacting a feedstock directly with a proteinaceous preparation immobilized on and within the pores of a support medium comprising the steps of:
    (a) forming a support medium having a thickness in the range of about 15 mils to about 35 mils and a first surface and a second surface and a plurality of random pores having pore sizes in the range of about 0.01 micron to about 100 microns extending from said first surface and said second surface:
    (b) positioning a flexible spacing means on said second surface of said support medium;
    (c) winding said support medium and said flexible spacing means upon a porous core means to form a jelly roll-like spiral ocnfiguration wherein said support means is not folded upon itself prior to being wound about said core means:
    (d) coupling first means to said core means; and
    (e) coupling second means to said free end of said spiral configuration.

9. The method of claim 8, further comprising the step of selecting the thickness of said flexible spacing means to permit desired flow of a selected feedstock through said reactor.

10. A reactor as defined in claim 1, further comprising: first coupling means coupled to said first means to introduce a feedstock to said core means and second coupling means coupled to said second means to remove the reacted feedstock from said free end of said spiral configuration.

* * * * *

UNITED STATES PATENT AND TRADEMARK OFFICE
CERTIFICATE OF CORRECTION

PATENT NO. : 4,689,302

DATED : August 25, 1987

INVENTOR(S) : Goldberg et al.

It is certified that error appears in the above—identified patent and that said Letters Patent is hereby corrected as shown below:

In the Abstract:

Line 8 (4th sentence), change "reactors" to --reactor--.

In the Specification:

Col. 2, line 5, change "pourous" to --porous--.

line 13, change "inveniton" to --invention--.

Col. 4, line 3, change "coverted" to --converted--.

line 8, delete "and".

line 48, change "the" to --The--.

Col. 5, line 35, change "if" to --of--.

Col. 1, line 24, delete "introduced" and substitute the words --introduction into--.

Col. 2, line 39, change "raise" to --raised--.

UNITED STATES PATENT AND TRADEMARK OFFICE
CERTIFICATE OF CORRECTION

PATENT NO. : 4,689,302                    Page 2 of 2
DATED      : August 25, 1987
INVENTOR(S): Goldberg et al.

It is certified that error appears in the above—identified patent and that said Letters Patent is hereby corrected as shown below:

In the Claims:

Col. 6, line 35, after "means" insert --and--.

line 38, change "0.003"." to --0.030".--.

line 52, change "ocnfiguration" to --configuration--.

Signed and Sealed this

Third Day of May, 1988

*Attest:*

DONALD J. QUIGG

*Attesting Officer*    *Commissioner of Patents and Trademarks*